(12) United States Patent  (10) Patent No.: US 7,166,100 B2
Jordan et al.  (45) Date of Patent: Jan. 23, 2007

(54) BALLOON CATHETER SHAFT DESIGN

(75) Inventors: Amanda Jordan, Pembroke Pines, FL (US); Darren Sherman, Fort Lauderdale, FL (US); Robert Slazas, Miami, FL (US); Stephen West, Pembroke Pines, FL (US)

(73) Assignee: Cordis Neurovascular, Inc., Miami Lakes, FL (US)

( * ) Notice: Subject to any disclaimer, the term of this patent is extended or adjusted under 35 U.S.C. 154(b) by 108 days.

(21) Appl. No.: 10/879,861

(22) Filed: Jun. 29, 2004

(65) Prior Publication Data

US 2005/0288628 A1  Dec. 29, 2005

(51) Int. Cl.
*A61M 25/00* (2006.01)

(52) U.S. Cl. .................. 604/525; 604/524; 604/527
(58) Field of Classification Search ........ 604/523–527, 604/103.01, 104.01, 264
See application file for complete search history.

(56) References Cited

U.S. PATENT DOCUMENTS

| 4,646,719 A |   | 3/1987  | Neuman et al. |         |
|-------------|---|---------|---------------|---------|
| 5,254,090 A |   | 10/1993 | Lombardi et al. |       |
| 5,254,107 A |   | 10/1993 | Soltesz       |         |
| 5,454,795 A | * | 10/1995 | Samson        | 604/526 |
| 5,460,608 A |   | 10/1995 | Lodin et al.  |         |
| 5,549,552 A |   | 8/1996  | Peters et al. |         |
| 5,759,173 A |   | 6/1998  | Preissman et al. |      |
| 5,823,995 A |   | 10/1998 | Fitzmaurice et al. |    |
| 5,843,032 A | * | 12/1998 | Kastenhofer   | 604/103.06 |
| 5,891,110 A |   | 4/1999  | Larson et al. |         |
| 5,891,112 A |   | 4/1999  | Samson        |         |
| 5,906,606 A |   | 5/1999  | Chee et al.   |         |
| 5,961,510 A |   | 10/1999 | Fugoso et al. |         |
| 5,971,975 A |   | 10/1999 | Mills et al.  |         |
| 6,004,310 A |   | 12/1999 | Bardsley et al. |       |
| 6,048,338 A |   | 4/2000  | Larson et al. |         |
| 6,152,912 A | * | 11/2000 | Jansen et al. | 604/526 |
| 6,165,163 A |   | 12/2000 | Chien et al.  |         |
| 6,217,565 B1 |  | 4/2001  | Cohen         |         |
| 6,254,588 B1 |  | 7/2001  | Jones et al.  |         |
| 6,273,879 B1 |  | 8/2001  | Keith et al.  |         |
| 6,344,029 B1 |  | 2/2002  | Estrada et al. |        |
| 6,464,684 B1 |  | 10/2002 | Galdonik      |         |
| 6,475,209 B1 | * | 11/2002 | Larson et al. | 604/525 |
| 6,488,655 B1 | * | 12/2002 | Wantink et al. | 604/103.9 |
| 6,500,147 B2 |  | 12/2002 | Omaleki et al. |        |
| 6,508,805 B1 |  | 1/2003  | Garabedian et al. |     |

(Continued)

*Primary Examiner*—Manuel Mendez
*Assistant Examiner*—Aamer S. Ahmed
(74) *Attorney, Agent, or Firm*—Michael W. Montgomery

(57) ABSTRACT

A balloon catheter for medical treatment of a patient, including therapeutic dilatation or deployment of medical devices such as stents or grafts. The balloon catheter has an "over-the-wire" configuration, including a proximal hub defining an inflation port and a guidewire port, a flexible shaft defining an inflation lumen and a guidewire lumen, a balloon near a distal end of the catheter, and a distal guidewire port. At least a portion of the shaft has an inner tubular body defining at least a portion of the guidewire lumen, surrounded by an outer tubular body defining at least a portion of the inflation lumen. A proximal portion of the inner body is reinforced by a hypotube, which provides much greater column strength and torsional stiffness. A distal end of the hypotube provides a graduated flexibility transition with a distal spiral-cut segment, in which the pitch of the spiral cut pattern decreases to provide increasing flexibility.

8 Claims, 5 Drawing Sheets

U.S. PATENT DOCUMENTS

| | | |
|---|---|---|
| 6,629,952 B1 | 10/2003 | Chien et al. |
| 6,635,047 B2 | 10/2003 | Forsberg |
| 6,638,245 B2 | 10/2003 | Miller et al. |
| 6,652,508 B2 * | 11/2003 | Griffin et al. ............... 604/526 |
| 6,659,977 B2 | 12/2003 | Kastenhofer |
| 6,663,614 B1 | 12/2003 | Carter |
| 6,702,782 B2 | 3/2004 | Miller et al. |
| 6,702,802 B1 | 3/2004 | Hancock et al. |
| 6,858,024 B1 * | 2/2005 | Berg et al. ................... 604/525 |
| 2003/0199914 A1 | 10/2003 | Diaz |

* cited by examiner

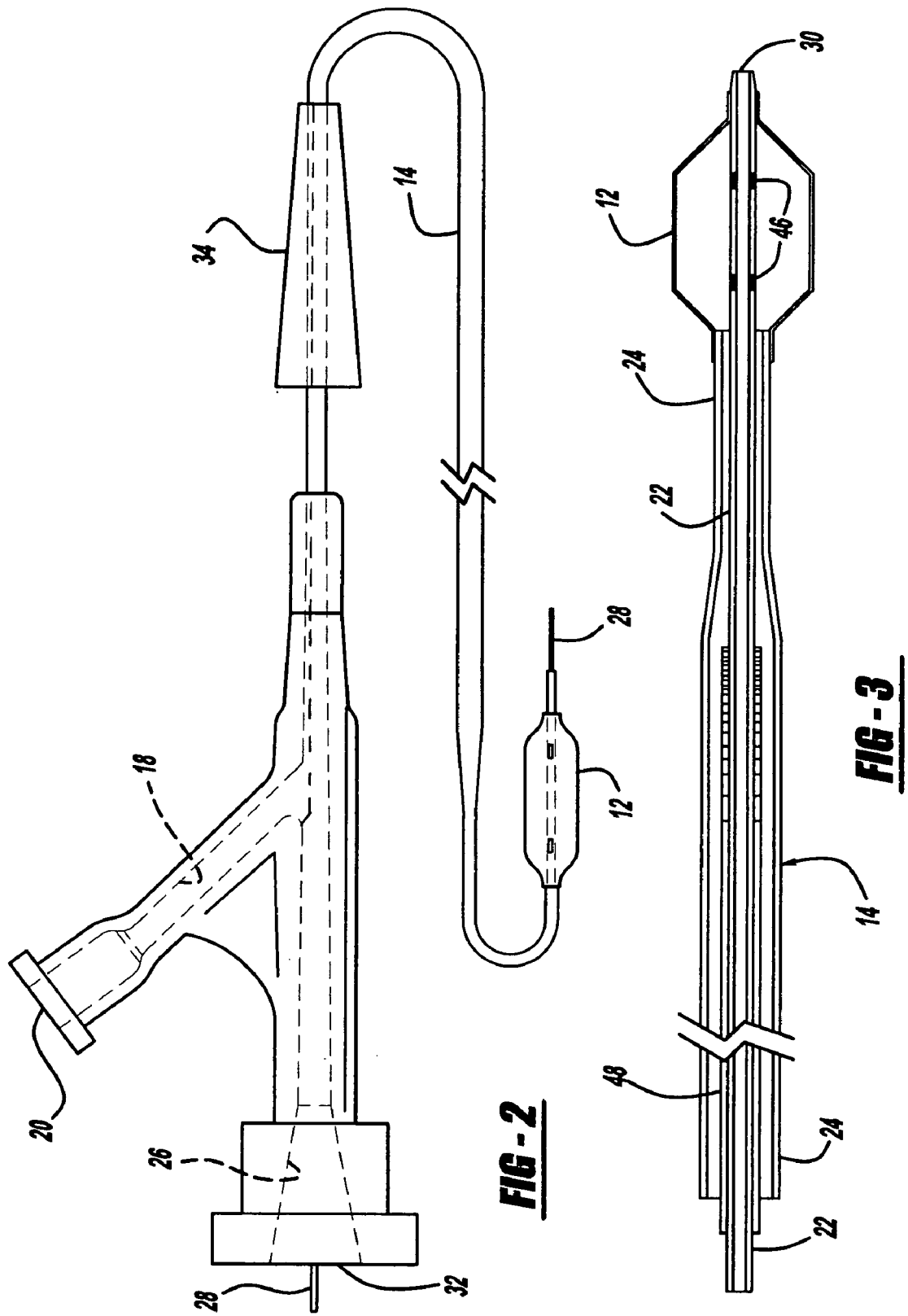

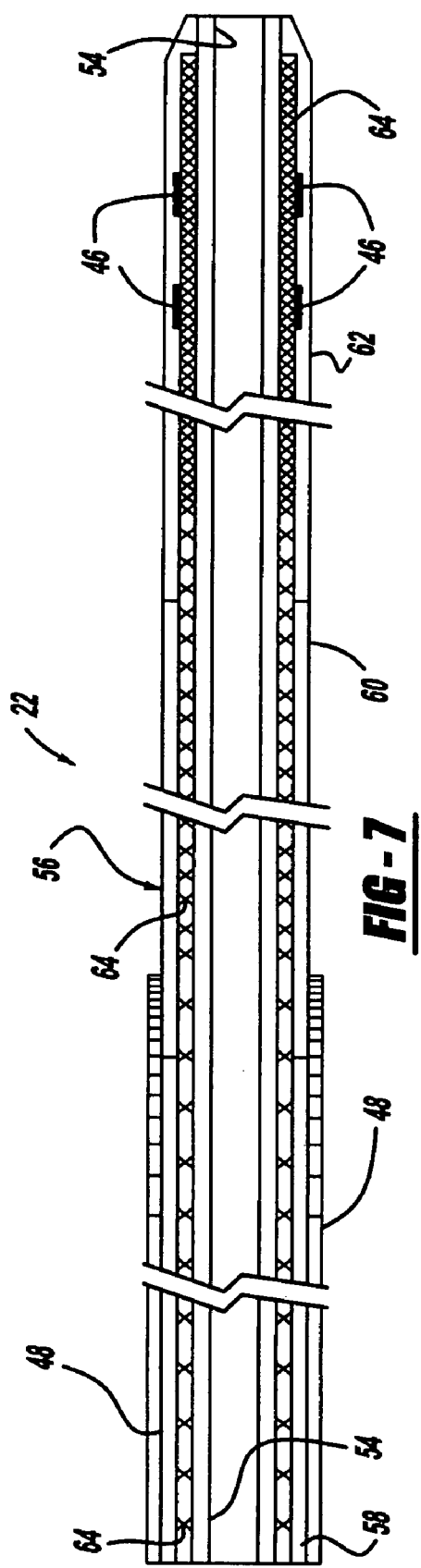
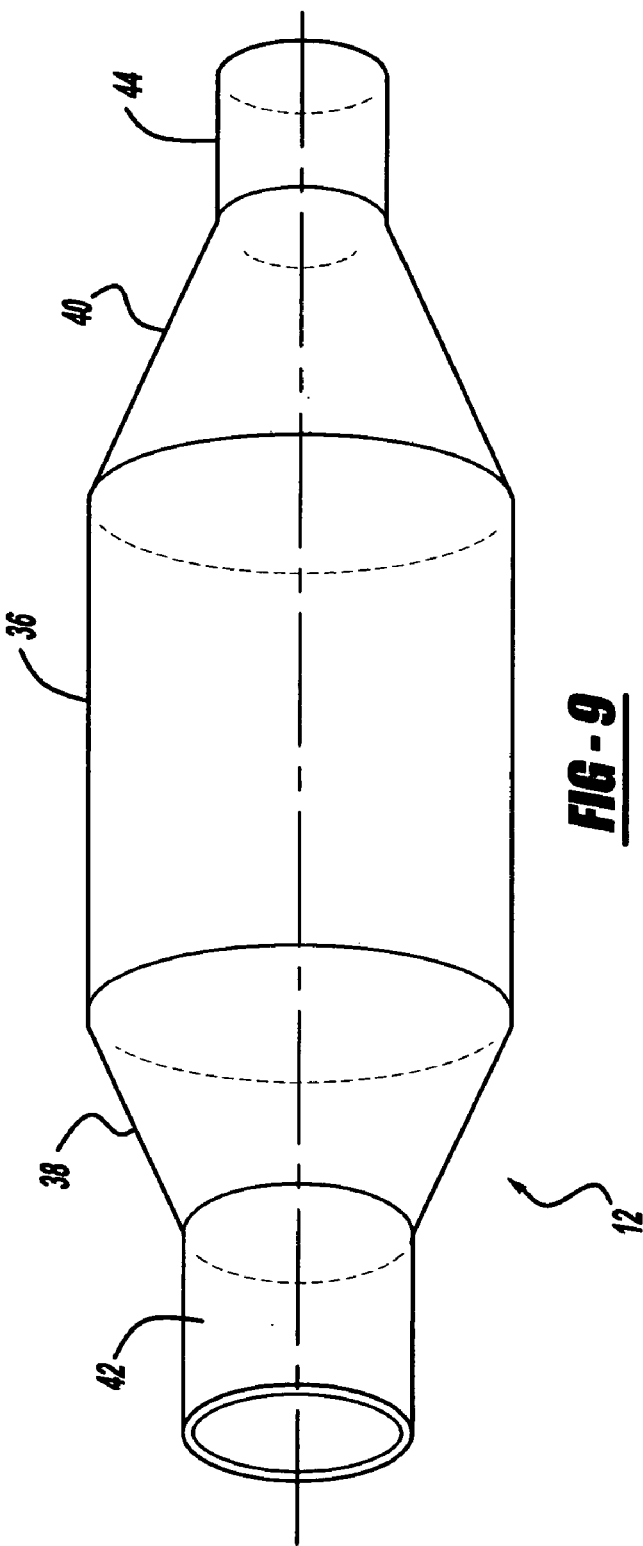

BALLOON CATHETER SHAFT DESIGN

BACKGROUND AND SUMMARY OF THE INVENTION

1. Technical Background

The present invention relates generally to medical devices, and more particularly to a balloon catheter having a shaft reinforced with a hypotube.

2. Discussion

Balloon catheters are used in a variety of therapeutic applications, including intravascular catheters for procedures such as angioplasty and/or deploying medical devices such as stents. Approximately one million angioplasties are performed worldwide each year to treat vascular disease, including coronary, peripheral and neurological blood vessels partially or totally blocked or narrowed by a lesion, stenosis, thrombosis, and/or vasospasm. By way of example, the present invention will be described in relation to coronary, peripheral and neurological angioplasty treatments. However, it should be understood that the present invention relates to any balloon catheter having a shaft reinforced with a hypotube according to the present invention as recited in the following claims, and is not limited to angioplasty, or stents, or even use in blood vessels.

Most balloon catheters have a relatively long and flexible tubular shaft defining one or more passages or lumens, and have an inflatable balloon attached near one end of the shaft. This end of the catheter where the balloon is located is customarily referred to as the "distal" end, while the other end is called the "proximal" end. The proximal end of the shaft is generally coupled to a hub, which defines a proximal inflation port and a proximal guidewire port. The proximal inflation port communicates with an inflation lumen defined by the shaft, which extends and is connected to the interior of the balloon, for the purpose of selectively inflating and deflating the balloon.

The proximal guidewire port communicates with a guidewire lumen defined by the shaft, for slidingly receiving a guidewire. The guidewire lumen extends between the proximal guidewire port in the hub at the catheter proximal end, and a distal guidewire port at the distal end of the catheter. The catheter of the present invention has an "over-the-wire" configuration in which the guidewire lumen extends essentially the full length of the catheter, between the proximal hub and the catheter distal end.

In general, balloon catheters according to the present invention have a shaft, of which at least a portion includes tubular inner and outer bodies, and a portion of the inner body is reinforced with a hypotube. The hypotube reinforcement has a spiral-cut segment at its distal end, to provide a smooth transition of flexibility from the hypotube-reinforced portion to a remainder of the shaft.

The balloon itself may define an inflatable central portion defining an inflated size, flanked by a pair of proximal and distal conical portions, flanked by a pair of proximal and distal legs or collars. The proximal and distal collars may be affixed to the shaft.

This disclosure of the present invention will include various possible features and embodiments. However, the present invention scope is set forth in each of the claims, and is not limited to the particular arrangements described in this disclosure.

An example of this type of over-the-wire balloon catheter is shown in the following patent, which is co-owned with the present invention: U.S. Pat. No. 5,370,615, entitled "Balloon Catheter For Angioplasty," issued to Johnson on Dec. 6, 1994.

Common treatment methods for using such a balloon catheter include advancing a guidewire into the body of a patient, by directing the guidewire distal end percutaneously through an incision and along a body passage until it is located within or beyond the desired site. The term "desired site" refers to the location in the patient's body currently selected for treatment by a health care professional. The guidewire may be advanced before, or simultaneously with, a balloon catheter. When the guidewire is within the balloon catheter guidewire lumen, the balloon catheter may be advanced or withdrawn along a path defined by the guidewire. After the balloon is disposed within the desired site, it can be selectively inflated to press outward on the body passage at relatively high pressure to a relatively constant diameter, in the case of an inelastic or non-compliant balloon material.

This outward pressing of a constriction or narrowing at the desired site in a body passage is intended to partially or completely re-open or dilate that body passageway or lumen, increasing its inner diameter or cross-sectional area. In the case of a blood vessel, this procedure is referred to as angioplasty. The objective of this procedure is to increase the inner diameter or cross-sectional area of the vessel passage or lumen through which blood flows, to encourage greater blood flow through the newly expanded vessel. The narrowing of the body passageway lumen is called a lesion or stenosis, and may be formed of hard plaque or viscous thrombus.

Some balloon catheters are used to deliver and deploy stents or other medical devices, in a manner generally known in the art. Stents, for example, are generally tubular scaffolds for holding a vessel or body passage open.

It is desirable to provide a balloon catheter having an optimum combination of various performance characteristics, which may be selected among: flexibility, lubricity, pushability, trackability, crossability, low profile and others. Flexibility may relate to bending stiffness of a medical device (balloon catheter and/or stent, for example) in a particular region or over its entire length, or may relate to the material hardness of the components. Lubricity may refer to reducing friction by using low-friction materials or coatings. Pushability may relate to the column strength of a device or system along a selected path. Trackability may refer to a capability of a device to successfully follow a desired path, for example without prolapse. Crossability may be clarified by understanding that physicians prefer to reach the desired site with the balloon catheter while encountering little or no friction or resistance. Profile may refer to a maximum lateral dimension of the balloon catheter, at any point along its length.

The balloon catheter of the present invention provides various advantages, which may include: pushability, optimized flexibility along the catheter length, torsional strength, pull strength, low profile, etc. Some embodiments of the present invention may also provide additional benefits, including smooth transitions in flexibility, lubricious guidewire lumen, etc.

In contrast to a distal shaft portion, the proximal portion of the shaft reinforced by the hypotube may have much greater column strength, which will tend to enhance the pushability of the balloon catheter, yet without adversely affecting flexibility in the distal portion of the shaft where flexibility is relatively more important.

BRIEF DESCRIPTION OF THE DRAWINGS

FIG. 2 is a side elevation view of a balloon catheter;

FIG. 3 is a longitudinal cross-section view of some components of a balloon catheter;

FIG. 7 is a longitudinal cross-section view of a tubular inner body;

FIG. 9 is a side elevation view of a balloon component.

DETAILED DESCRIPTION OF THE PREFERRED EMBODIMENT

The following description of the preferred embodiments of the present invention is merely illustrative in nature, and as such it does not limit in any way the present invention, its application, or uses. Numerous modifications may be made by those skilled in the art without departing from the true spirit and scope of the invention.

Figure 1:
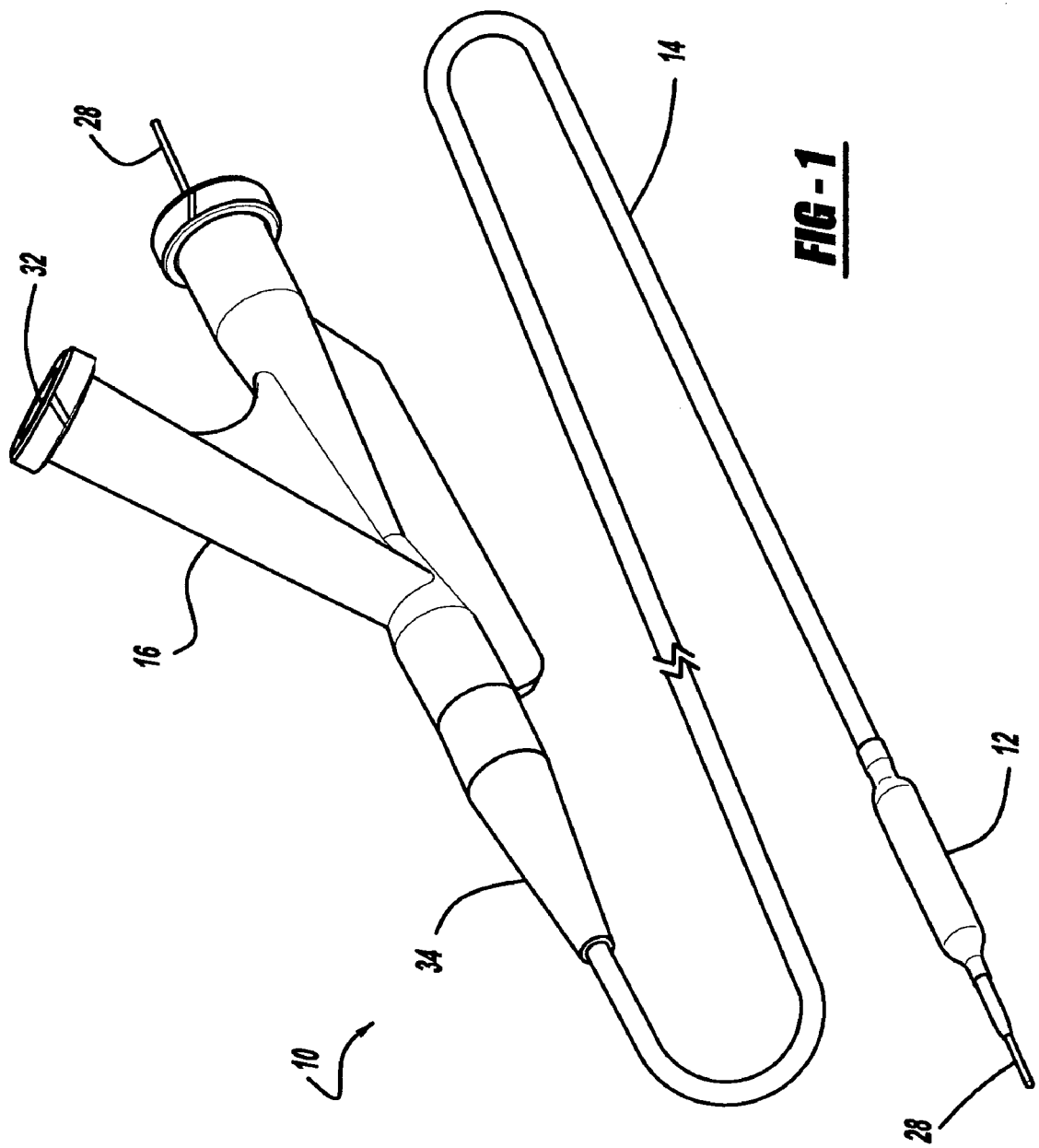
FIG. 1 is an external perspective view of a balloon catheter.

Referring to the drawings, a balloon catheter is depicted, with one of the preferred embodiments of the present invention being shown at reference number 10 in FIG. 1. The balloon catheter of FIG. 1 has an inflatable balloon 12, a relatively long and flexible tubular shaft 14, and a hub 16. The balloon 12 is affixed to the shaft 14 near a distal end of the shaft 14, and the hub 16 is affixed to the proximal end of the shaft 14.

The shaft defines at least two passages or lumens, one of which is an inflation lumen 18 connected to the balloon 12 for selectively inflating and deflating the balloon 12. The inflation lumen 18 thus provides fluid communication between the interior of the balloon 12 at the distal end of the inflation lumen 18, and a hub inflation port 20 having a coupling or luer-lock fitting at the proximal end for connecting the inflation lumen to a source of pressurized inflation fluid (not shown) in the conventional manner.

A second lumen defined by the catheter 10 is a guidewire lumen 26 is adapted to receive an elongated flexible guidewire 28 in a sliding fashion. The guidewire 28 and catheter 10 may thus be advanced or withdrawn independently, or the catheter 10 may be guided along a path selected with the guidewire 28.

In the illustrated embodiment, shaft 14 is constructed of an inner and outer tubular body 22 and 24. The inner body 22 defines the guidewire lumen 26, while inflation lumen 18 is defined by an annular space between the inner and outer tubular bodies 22 and 24. The guidewire lumen 26 extends through the inner tubular body 22 from a distal guidewire port 30 near the catheter distal end to a proximal guidewire port 32 defined by hub 16.

A flexible tubular strain relief 34 surrounds shaft 14 at a transition between the shaft 14 and hub 16. Strain relief 34 is affixed to shaft 14 and/or hub 16 in any desired manner.

The balloon 12 shown in FIGS. 1, 2, 3, and 9 has a central portion 36 defining an inflated size and a working length, flanked by a pair of tapering conical segments 38 and 40, flanked by a pair of "legs" or collars 42 and 44. Proximal collar 42 is affixed to outer body 24 near its distal end, and distal collar 44 is affixed to inner body 22 near its distal end.

FIG. 3 shows inner body 22, outer body 24, and balloon 12. A pair of radiopaque markers 46 indicate the position of the central working length portion of the balloon to a physician using x-ray video.

A proximal portion of inner body 22 is reinforced with a hypotube 48 component. The hypotube 48 is affixed to and surrounds a portion of inner body 22, extending from proximal hub 16 along a proximal segment of the shaft 14. Hypotube 48 has a cylindrical segment 50 and a spiral-cut segment 52.

Figure 5:
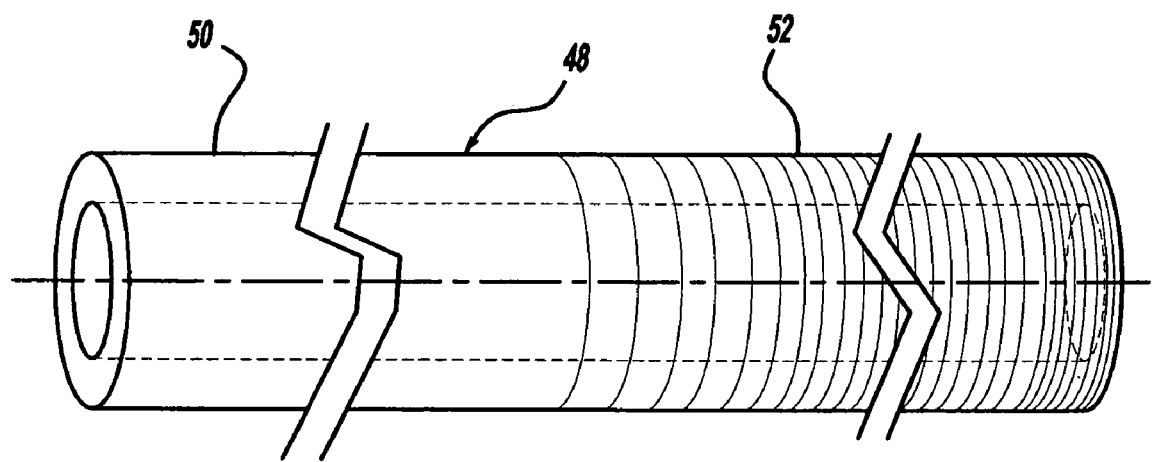
FIG. 5 is a side elevation view of a hypotube component.

Spiral-cut segment 52 provides a graduated transition in bending flexibility. The spiral pattern cut into hypotube may have a pitch that changes, to increase flexibility in specific areas. For example, the longitudinal distance between adjacent coils of the spiral cut path may become shorter as the spiral cut progresses from its proximal beginning to the distal end of the hypotube, as shown in FIG. 5. In other words, the spiral cuts are closer together at the distal end of the hypotube, and farther apart at the proximal end of the spiral cut.

Figure 6:
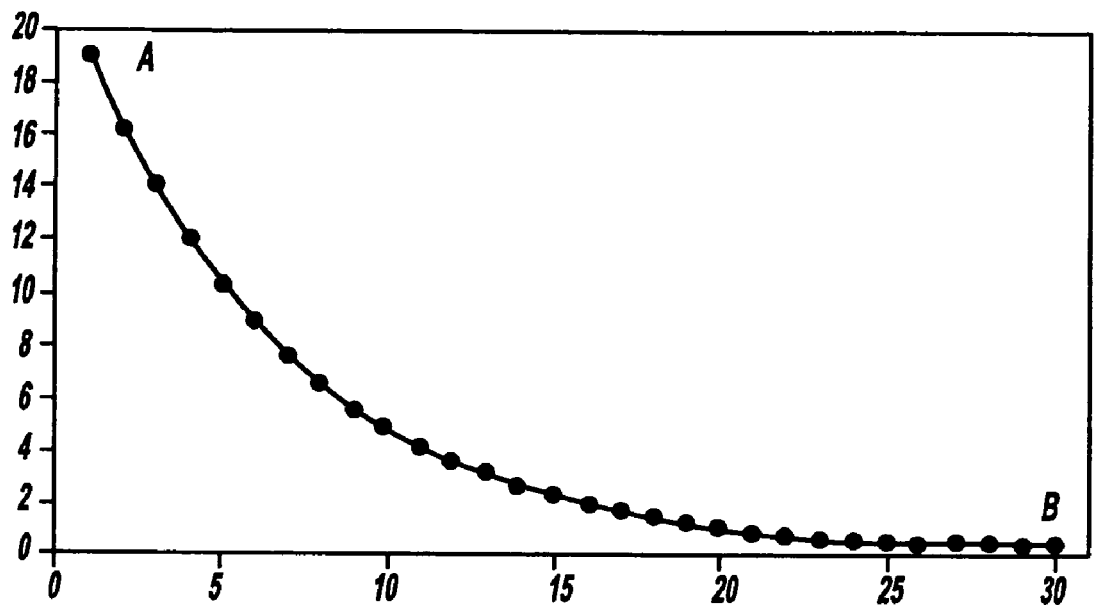
FIG. 6 is a graph showing a possible pitch curve for a spiral-cut segment of a hypotube component.

As a result, the distal end of the hypotube is more flexible than the proximal portion of the hypotube. This transition in flexibility may be accomplished in various ways. For example, the pitch of the spiral cut may have a proximal pitch, proceeding in a linear fashion down to a smaller distal pitch. In another example, the pitch of the spiral cut may decrease from a proximal pitch A to a distal pitch B in a non-linear manner, as depicted in FIG. 6. In the example of FIG. 6, an exponential progression has been selected. Other non-linear pitch curves may be selected.

One particular example of an inner tubular body 22 is shown in FIG. 7. In this example, the inner body tube 22 has a multi-layer construction. The inner layer 54 is a lubricious polymer material, such as for example high density polyethylene (HDPE) or polytetrafluoroethylene (PTFE). The outer layer 56 is a strong polymer material, which is selected to bond well with the material(s) selected for the hub 16 and the balloon 12. Examples of acceptable materials are nylons or polyether block amide (PEBA). In the specific example shown in FIG. 7, the outer layer 56 has multiple segments of differing flexibility. For example, FIG. 7 shows a proximal, middle, and distal segment of outer layer material 58, 60 and 62, arranged in order of increasing flexibility from the proximal to the distal direction.

In addition, the example shown in FIG. 7 has an internal reinforcement in the form of braid 64. The braided reinforcement is depicted in a diagrammatic manner for clarity, and may be at least a pair of wires coiled around inner body 22, between the inner and outer layers 54 and 56, in a criss-crossing fashion. The braid wires 64 may be a metal such as stainless steel, or another strong material such as Kevlar fibers. In the example of FIG. 7, the braid wires 64 are arranged with a pitch that decreases in the distal direction. In other words, the wraps of the braid wires are closer together near the distal end of inner body than at the proximal end. This decreasing pitch, measured in increasing wires per inch, may be arranged progressively along the length of the inner body, in linear or non-linear fashion, or in specific segments, illustrated in FIG. 8. The braid segments in FIG. 7 may be arranged to align with the segments of different flexibility of the outer layer material, but need not be so aligned, as shown in FIG. 7.

Figure 8:
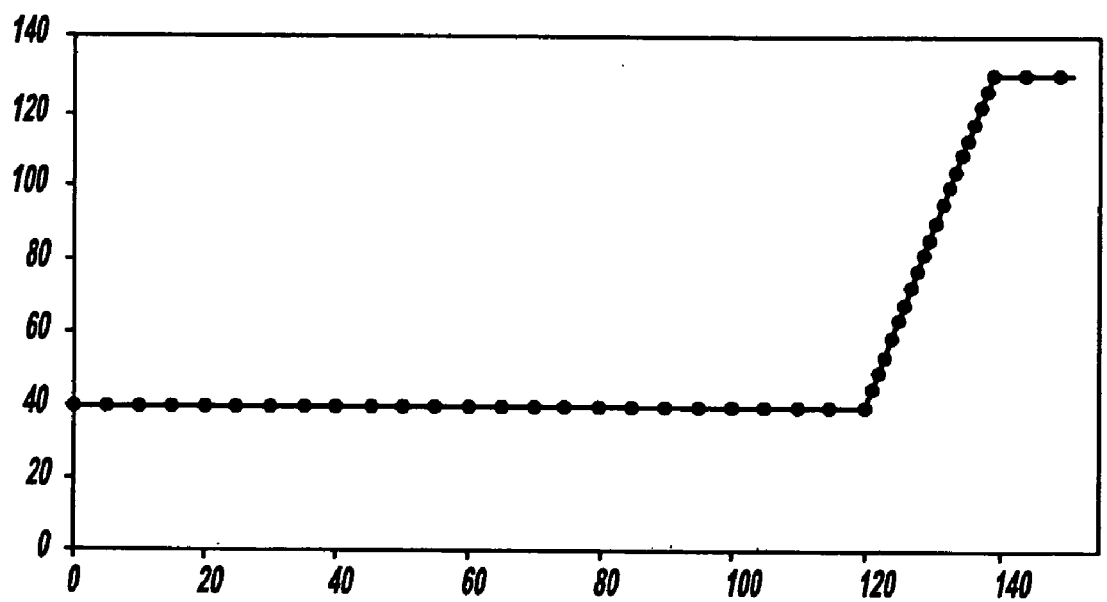
FIG. 8 is a graph showing a possible pitch curve for a braided reinforcement.

FIG. 8 shows the number of braid wires per inch, along the length of inner body 22. Of course, other curves and arrangements may be selected.

If desired, inner body may be provided with radiopaque markers, to indicate specific locations on the catheter to a physician using an x-ray video. In the example of FIG. 7, a pair of marker bands 66 made of a radiopaque material such as for example tungsten, platinum, etc. are provided near the distal end of the inner body. The markers may be placed on the outside of inner body, or between the inner and outer layers, as shown in FIG. 7

The distal end of inner body may be arranged to form part of the distal tip of the catheter. If so, it should be optimally shaped at some point during construction of the catheter, as shown in FIG. 7.

The inner surface of tubular inner body defines at least a portion of the guidewire lumen. To enhance ease of operation, this inner surface may be of a material selected for high lubricity, which will present low frictional resistance to movement of a guidewire inserted within guidewire lumen. Some prior catheters have used an inner layer defining a guidewire lumen that is made of Teflon®, or PTFE, and it is possible to likewise use PTFE in a catheter according to the present invention.

Another possibility is to use a different material for the guidewire lumen. Because many guidewires have a PTFE coating, in some operating conditions, it is possible that the resulting interface between similar materials, PTFE tube on PTFE-coated guidewire, to exhibit a slight "slip stiction" effect. Accordingly, another lubricant material may be used, for example HDPE, as the inner layer of inner body. The markers may be placed around the outside of the inner body, or inside the wall of the inner body. In FIG. 7, marker bands 66 are placed between inner and outer layers 54 and 56 of inner body 22.

Figure 4:
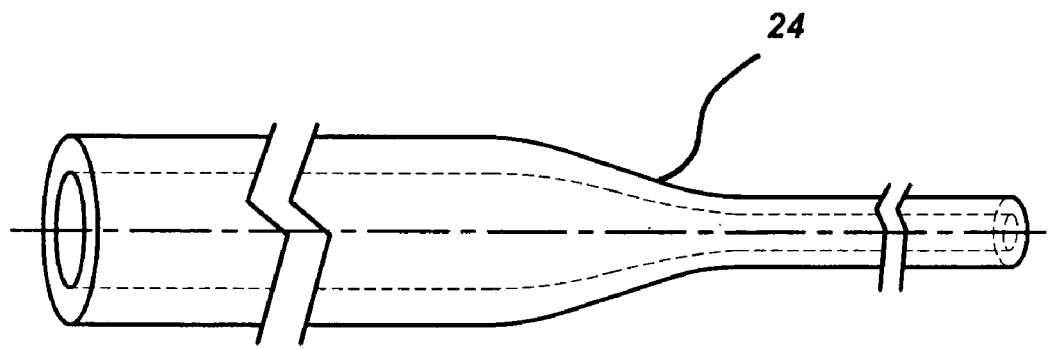
FIG. 4 is a side elevation view of a tubular outer body component.

The outer body 24 may be a conventional polymer tube or a more sophisticated construction. An example outer body 24 is depicted in FIG. 4, in which the outer body tube 24 tapers from a proximal size to a smaller distal size. In particular, outer body 24 of FIG. 4 is a bump extrusion, in which the outer size and inner size (and therefore the wall thickness) draws down and narrows simultaneously along the length of the outer body 24.

The hypotube may be made of metal which is selected to be biocompatible, such as for example stainless steel. Other acceptable metals may include nitinol, titanium, etc.

The inflation lumen 18 extends from the inflation port 20, through a proximal portion of the inflation lumen 18 defined by the hypotube, through a distal portion of the inflation lumen 18 defined by the annular space between the inner and outer bodies 22 and 24, and into the balloon.

The balloon catheter and stent delivery system of the present invention may be made using various methods, including extruding polymer tubes, injection-molding the proximal hub, and extruding a balloon parison and then blowing the parison into a balloon having the desired properties. It is also possible to affix polymer components to each other by heat-sealing, or by using an adhesive such as a UV-cured adhesive.

It should be understood that an unlimited number of configurations for the present invention could be realized. The foregoing discussion describes merely exemplary embodiments illustrating the principles of the present invention, the scope of which is recited in the following claims.

Those skilled in the art will readily recognize from the description, claims, and drawings that numerous changes and modifications can be made without departing from the spirit and scope of the invention.

What is claimed is:

1. A balloon catheter having a proximal end and a distal end, for medically treating a patient, comprising:
   a balloon defining an interior;
   a hub defining a proximal inflation port and a proximal guidewire port;
   a flexible shaft having a proximal and distal end; the shaft extending between the balloon and hub, the shaft defining an inflation lumen extending from the proximal inflation port to the interior of the balloon, the shaft defining a guidewire lumen extending from the proximal guidewire port to a distal guidewire port near the distal end of the catheter; the hub being affixed to the proximal end of the shaft, and the balloon being affixed to the shaft near its distal end;
   at least a portion of the shaft including an inner tubular body and an outer tubular body, each having a proximal and distal end; the outer body surrounding at least a portion of the inner body;
   wherein the inner body has an inner layer and an outer layer of polymer materials portions of the outer layer having different flexibilities;
   a portion of the inner body is reinforced by a hypotube having a proximal and distal end; a distal portion of the hypotube having a spiral cut to increase flexibility of the hypotube; the pitch of the spiral cut decreasing in the distal direction, from a larger proximal pitch to a smaller distal pitch, providing a transition in flexibility between the portions of the shaft that extend proximal and distal of the spiral cut of the hypotube;
   wherein the hypotube surrounds and is affixed to a portion of the inner body;
   wherein the inner body has braided reinforcement extending between the inner and outer layers from a proximal position to a distal position;
   wherein an amount of braid per longitudinal distance increases from a proximal position to a distal position; and
   wherein the hypotube distal end, and at least one transition between flexibilities of the outer layer material, and at least one tansition between the amount of braid per distance, are each located at different positions.

2. The balloon catheter of claim 1, wherein the pitch of the spiral cut decreases in a non-linear fashion.

3. The balloon catheter of claim 1, wherein the pitch of the spiral cut decreases exponentially.

4. The balloon catheter of claim 1, wherein the outer body has an outer dimension and an inner dimension which both decrease from a proximal position to a distal position.

5. The balloon catheter of claim 1, wherein the inner layer and outer layer are of different polymer materials, the inner layer being lubricious.

6. The balloon catheter of claim 5, wherein the inner layer is PTFE.

7. The balloon catheter of claim 5, wherein the inner layer is HDPE.

8. The balloon catheter of claim 5, wherein the inner layer has a melting temperature less than a melting temperature of the outer layer.

* * * * *